US010365189B2

(12) United States Patent
Wheeler

(10) Patent No.: US 10,365,189 B2
(45) Date of Patent: *Jul. 30, 2019

(54) HISTOLOGICAL SPECIMEN TREATMENT

(71) Applicant: Steven Wheeler, Gardena, CA (US)

(72) Inventor: Steven Wheeler, Gardena, CA (US)

(\*) Notice: Subject to any disclaimer, the term of this patent is extended or adjusted under 35 U.S.C. 154(b) by 146 days.

This patent is subject to a terminal disclaimer.

(21) Appl. No.: 14/706,389

(22) Filed: May 7, 2015

(65) Prior Publication Data

US 2016/0327457 A1    Nov. 10, 2016

(51) Int. Cl.
G01N 1/30 (2006.01)
C08K 5/00 (2006.01)
C08F 220/20 (2006.01)
C08F 220/28 (2006.01)
C08K 5/12 (2006.01)

(52) U.S. Cl.
CPC ............ *G01N 1/30* (2013.01); *C08F 220/20* (2013.01); *C08F 220/28* (2013.01); *C08K 5/0016* (2013.01); *C08K 5/12* (2013.01); *C08F 2220/281* (2013.01); *C08F 2800/20* (2013.01); *G01N 2001/307* (2013.01)

(58) Field of Classification Search
CPC ....... G01N 1/30; C08K 220/28; C08K 5/0016
See application file for complete search history.

(56) References Cited

U.S. PATENT DOCUMENTS

| 2,150,757 | A | 3/1939 | Bodine |
| 2,684,925 | A | 7/1954 | Ferrari |
| 3,389,052 | A | 6/1968 | Theodore |
| 3,456,300 | A | 7/1969 | Pickett |
| 3,546,334 | A | 12/1970 | Lerner |
| 3,674,040 | A | 7/1972 | Howells |
| 3,892,197 | A | 7/1975 | Kinney et al. |
| 3,961,097 | A | 6/1976 | Gravlee |
| 3,995,022 | A | 11/1976 | Heanley |
| 4,099,483 | A | 7/1978 | Henderson |
| 4,141,312 | A | 2/1979 | Louder |
| 4,199,558 | A | 4/1980 | Henderson |
| 4,221,823 | A | 9/1980 | Pearson |
| 4,300,243 | A | 11/1981 | Baumgartner |
| 4,545,831 | A | 10/1985 | Ornstein |
| 4,569,647 | A | 2/1986 | McCormick |
| 4,656,047 | A | 4/1987 | Kok |
| 4,670,386 | A | 6/1987 | Sugaar |
| 4,681,996 | A | 7/1987 | Collins |
| 4,784,873 | A | 11/1988 | Kienecker |
| 4,835,354 | A | 5/1989 | Collins |
| 4,839,194 | A | 6/1989 | Malluche |
| 4,882,128 | A | 11/1989 | Hukvari |
| 4,891,239 | A | 1/1990 | Dudley |
| 4,911,915 | A | 3/1990 | Fredenburgh |
| 4,992,763 | A | 2/1991 | Bert |
| 4,994,237 | A | 2/1991 | Login |
| 5,023,187 | A | 6/1991 | Koebler |
| 5,030,929 | A | 7/1991 | Moeller |
| 5,049,510 | A | 9/1991 | Repasi |
| 5,068,086 | A | 11/1991 | Sklenak |
| 5,089,288 | A | 2/1992 | Berger |
| 5,104,640 | A | 4/1992 | Stokes |
| 5,122,633 | A | 6/1992 | Moshammer |
| 5,230,865 | A | 7/1993 | Hargett |
| 5,244,787 | A | 9/1993 | Key |
| 5,256,571 | A | 10/1993 | Hurley |
| 5,289,140 | A | 2/1994 | Jorgenson |
| 5,318,795 | A | 6/1994 | Stokes |
| 5,387,397 | A | 2/1995 | Strauss |
| 5,401,625 | A | 3/1995 | Robinson |
| 5,431,952 | A | 7/1995 | Ocello |
| 5,432,056 | A | 7/1995 | Hartman |
| 5,460,797 | A | 10/1995 | Ryan |
| 5,532,462 | A | 7/1996 | Butwell |
| 5,609,820 | A | 3/1997 | Bridges |
| 5,625,706 | A | 4/1997 | Lee |
| 5,672,696 | A | 9/1997 | Wang |
| 5,679,333 | A | 10/1997 | Dunphy |
| 5,712,605 | A | 1/1998 | Flory |
| 5,758,033 | A | 5/1998 | Bernstein |
| 5,782,897 | A | 7/1998 | Carr |
| 5,796,080 | A | 8/1998 | Jennings |
| 5,830,417 | A | 11/1998 | Kingston |
| 5,849,517 | A | 12/1998 | Ryan |
| 5,875,286 | A | 2/1999 | Bernstein |

(Continued)

FOREIGN PATENT DOCUMENTS

| DE | 4400815 A1 | 7/1995 |
| EP | 822403 B1 | 7/1998 |

(Continued)

OTHER PUBLICATIONS

Wester et al., Zinc-based fixative improves preservation of genomic DNA and proteins in histoprocessing of human tissues, Laboratory Investigation, vol. 83, p. 889-899, 2003.\*

(Continued)

*Primary Examiner* — Taeyoon Kim
*Assistant Examiner* — Tiffany M Gough
(74) *Attorney, Agent, or Firm* — Fish & Richardson P.C.

(57) ABSTRACT

A single dissolving compound forms plural azeotropes, which can be azeotropically vaporized off at various stages of the treatment process, thus maintaining predictable concentrations of the chemicals present. The treatment process can be performed in the absence of formalin or related compounds which can interfere with the preservation of genetic material. A process for preserving a specimen includes using a dissolving compound that can form a plural number of azeotropes, at least one azeotrope being formed between one or more components of the dissolving compound and specimen-supplied water, and at least one azeotrope being formed between different components of the dissolving compound; successively and azeotropically vaporizing off formed azeotropes; and impregnating the specimen with a support medium.

14 Claims, 9 Drawing Sheets

(56) References Cited

U.S. PATENT DOCUMENTS

| | | | |
|---|---|---|---|
| 6,011,247 | A | 1/2000 | Grillo |
| 6,042,874 | A | 3/2000 | Visinoni |
| 6,072,086 | A | 6/2000 | James |
| 6,183,995 | B1 | 2/2001 | Burmer |
| 6,204,375 | B1 | 3/2001 | Lader |
| 6,207,408 | B1 | 3/2001 | Essenfeld |
| 6,248,535 | B1 | 6/2001 | Danenberg |
| 6,258,329 | B1 | 7/2001 | Mutterer |
| 6,268,596 | B1 | 7/2001 | Lauf |
| 6,291,180 | B1 | 9/2001 | Chu |
| 6,404,906 | B2 | 6/2002 | Bacus |
| 6,586,713 | B2 | 7/2003 | Essenfeld |
| 6,615,763 | B2 | 9/2003 | Edwards |
| 6,674,884 | B2 | 1/2004 | Bacus |
| 6,681,035 | B1 | 1/2004 | Bamford |
| 6,793,890 | B2 | 9/2004 | Morales |
| 6,797,928 | B2 | 9/2004 | Giberson |
| 6,892,197 | B2 | 5/2005 | Eda |
| 6,930,292 | B1 | 8/2005 | Winther |
| 6,951,663 | B1 | 10/2005 | Edwards |
| 7,075,045 | B2 | 7/2006 | Visinoni |
| 2001/0051365 | A1 | 12/2001 | Morales |
| 2002/0177183 | A1 | 11/2002 | Giberson |
| 2005/0090017 | A1 | 4/2005 | Morales |
| 2009/0298172 | A1 | 2/2009 | Wheeler |
| 2012/0202241 | A1 | 8/2012 | Wheeler |
| 2016/0290900 | A1 | 10/2016 | Wheeler |

FOREIGN PATENT DOCUMENTS

| | | |
|---|---|---|
| EP | 562877 B1 | 6/2000 |
| EP | 680243 B1 | 1/2004 |
| WO | WO1986006479 A1 | 11/1986 |
| WO | WO1998005938 A1 | 2/1998 |
| WO | WO1999009390 A1 | 2/1999 |

OTHER PUBLICATIONS

Azeotropic Data for binary mixtures, 2014 blogs.uoregon.edu.*
Table 1 Binary organic azeotropes useful for solvent cleaning, Nov. 2004.*
Doherty et al., Distillation, Azeotropic and Extractive, vol. 8, p. 786-852. https://onlinelibrary.wiley.com/doi/pdf/10.1002/0471238961.0409192004150805.a01.pub2 (Year: 2000).*
'refractiveindex.info' [online]. "Hexane Refractive Index." 2005, [Retrieved on Aug. 9, 2017] Retrieved from the internet: URL<https://refractiveindex.info/?shelf=organic&book=hexane&page=Kozma>. 2 pages.
'refractiveindex.info' [online]. "Acetone Refractive Index." 1997. [Retrieved on Aug. 9, 2017] Retrieved from the internet: URL<https://refractiveindex.info/?shelf=organic&book=acetone&page=Rheims>. 2 pages.
United States Office Action in U.S. Appl. No. 15/180,285, dated Aug. 22, 2017, 17 pages.
Dimethyl sulfoxide (Retrieved on Sep. 24, 2012 from the Internet: <URL: http://www.sigmaaldrich.com/chemistry/solvents/dimethyl-sulfoxide-center/physical-properties.html>).
2-propanol (Retrieved on Sep. 24, 2012 from the Internet: URL: http://www.sigmaaldrich.com/chemistry/solvents/2propanol-center.html>).
Acetic Acid (Retrieved on Sep. 24, 2012 from the Internet: <URL: http://www.safcglobal.com/catalog/product/sial/a6283?null>).
Polyethylene glycol (Retrieved on Sep. 24, 2012 from the Internet: <URL: http://www.sigmaaldrich.com/etc/medialib/docs/Aldrich/Product_Information_Sheet/P2365pis.Par.0001.File.temp/p3265pis.pdf>).
Hexane (Retrieved on Sep. 25, 2012 from the Internet: <URL: http://www.signaaldrich.com/chemistry/solvents/hexane-center.html>).
Solvent Center, www.sigmaaldrich.com.
Liu et al. J. of Supercritical Fluids, 2006, 39:89-101.
Specific Gravity and Viscosity of Liquid, www.csgnetwork.com.
Non-final office action dated Aug. 17, 2011 from U.S. Appl. No. 12/128,523, 25 pages.
Non-final office action dated Oct. 11, 2012 from U.S. Appl. No. 13/396,541, 24 pages.
Final office action dated May 17, 2013 from U.S. Appl. No. 13/396,541, 27 pages.
Non-final office action dated Nov. 21, 2013 from U.S. Appl. No. 13/396,541, 10 pages.
Final office action dated Jul. 22, 2014 from U.S. Appl. No. 13/396,541, 10 pages.
Mujiburohman et al. "A preliminary study: Distillation of isopropanol-water mixture using fixed adsorptive distillation method." Separation and Purification Technology, Feb. 1, 2006, 48(1):85-92.
'pubchem.ncib.nlm.nih.gov.' [online] "Isopropanol C3H80—PubChem," Retrieved on Aug. 31, 2015 from the internet: <http://pubchem.ncbi.nlm.nih.gov/compound/isopropanol#section=Top>. 102 pages.

* cited by examiner

HISTOLOGICAL SPECIMEN TREATMENT

TECHNICAL FIELD

This invention relates to methods and instrumentation for the preservation of specimens for histological analysis.

BACKGROUND

U.S. Publication No. 2009/0298172 to Wheeler, hereby incorporated by reference in its entirety, describes a histoprocessing technique. Referring to prior art FIG. 1, the histoprocessing instrumentation 25 described in U.S. Publication No. 2009/0298172 includes a hermetically sealable, pressure and temperature regulated reaction container 11 sized to hold a number of tissue samples 26. The reaction container is connected by a network of conduits and valves to a source of melted Paraffin constituted by a Paraffin makeup vessel 27, to a source of dissolving compound in the form of a solvent regenerator 28 drawing from a chemical tank 29, to a solvent pump 30, to a vacuum pump 31, and to an overflow reservoir 32. The solvent pump is designed to operate over a wide range of temperatures and pressures.

As shown in prior art FIG. 2, the solvent regenerator 28 of U.S. Publication No. 2009/0298172 is connected to a solvent distillation assembly 33 including an accumulator 34, a recirculation pump 35 and a condenser 36. A thermocatalytic oxidizer 37 is used to breakdown waste gases into water and carbon dioxide. A carbon bed device could be substituted for the oxidizer. The waste material extracted from the used dissolving compound is sent to a waste tank 38. A process heater 39 (FIG. 1) is provided between the solvent pump 30 and the reaction vessel 11. A heat exchanger 60 consisting of a 500 watt, explosion-proof bulb is mounted inside the solvent regenerator 28. A jacket heater 40 surrounds the solvent regenerator 28. A similar jacket heater 65 surrounds the reaction container 11. A series of snubber protected pressure sensors 64, 72 and 73 are connected to various areas of the system to regulate pressures. Valves 41-59, and the pumps 30, 31 and 35 are controlled by a programmable electronic unit 41 according to techniques well known in the industrial process arts.

U.S. Publication No. 2009/0298172 describes a process of treating tissue specimens. Tissue specimens are loaded into a stainless steel or polymer constructed basket, and then placed into the reaction container 11. The container cover is then closed and latched. Proximity sensors detect the lid and the process starts. Valve 49 opens and the vacuum pump 31 is started. The pressure of the system is reduced below ambient atmospheric pressure. Valve 49 closes, the vacuum pump is turned off and the system comes to pressure equilibrium. If this condition is not achieved within one minute, a leak is assumed, and the system is shut off.

Preconditioned dissolving compound is transferred from the solvent regenerator 28 to the reaction container 11. Valves 43, 44 and 45 are opened and the reactor jacket heater 65 is energized. The solvent pump 30 and heater 39 are energized. Hot compound fills the reaction container until a solvent level detector switch 67 is triggered. The pressure in the reaction container is regulated by opening valve 47 and the reactor's pressure sensor 64. Valve 45 closes and valve 42 opens. The dissolving compound is recycled and heated in the closed loop consisting of valves 42, 43, and 44, heater 39, solvent pump 30, and the reaction container 11. At this time, the solvent pump 30 is used to pump up the reactor 11 to an operating pressure as high as about 3.3 bars (50 psig).

Specimens are exposed to the dissolving compound for 10 to 30 minutes. During this exposure, cellular solutes are extracted, (e.g., water, lipids, etc.), and replaced with a mixture of liquid Paraffin and the low molecular hydrocarbons of the compound. Valve 42, 43 and 44, the process heater 39, and the solvent pump 30 are turned off. Hot dissolving compound is transferred from the reaction container 11 to the solvent regenerator 28. The transfer path includes valves 42, 43, and 44. Valve 47 is opened between the reaction container and the solvent regenerator in order to equilibrate pressure. The transfer lasts until the container's low level indicator switch 63 is reset. At this time, valve 42 is closed and the compound is recycled and reconditioned as later explained. The reaction container 11 is next flooded with liquid Paraffin as follows. Valves 42 and 49 open, the vacuum pump 31 is turned on. Liquid Paraffin flows into the container until the level indicator switch 67 is triggered. A high level indicator switch 68 in the container acts as a fail-safe device. At this time valve 42 is closed. The saturated specimens are then subjected to a vacuum to extract volatiles.

The pressure in the container is further reduced to evaporate all dissolving compound present. The diffusion pump 66 is used to reduce pressures to less than 1 torr. Vacuum is applied until pressure equilibrium is achieved, e.g. about 0.9 to 0.99 At. (−27 to −29.91 inches Hg), depending upon solvent. Once equilibrium is reached, all volatile solvent molecules have been removed from the reaction container and specimens. The process is allowed to continue for an additional 10 to 30 minutes depending upon total mass of specimens.

The vacuum system consists of the vacuum pump 31, the diffusion pump 66, and the overflow vessel 32 equipped with a proximity sensor 71, and an isolation valve 49. The overflow vessel acts as an additional fail-safe device in case of failure of the high level indicator switch 68. The air makeup valve 50 is provided to dilute gases prior to entering the thermocatalytic oxidizer 37 and to supply cooling gases to the reaction container during cool down cycles. The pressure sensors 64, 72 and 73 are connected to the control unit 41 in order to monitor all processes of the instrument. Snubbers are employed to prevent liquid from entering the pressure sensors.

In a final step, the Paraffin is returned to the Paraffin makeup vessel 27 as follows. Valves 42, 49 and 50 are opened and the vacuum pump 31 is turned off. Cooling air is drawn through valve 50 and routed to the reaction container 11. Paraffin is gravitated to the Paraffin makeup vessel 27. During this time, the specimen temperature drops below the Paraffin melt point. The lid of the container opens, the specimen tray is withdrawn and the specimens are extracted and separated.

U.S. Publication No. 2009/0298172 describes that the following alternate batch solvent blending process may be practiced to prepare a Paraffin-loaded dissolving compound.

Referring to prior art FIG. 2, the reaction container 11 is hermetically sealed. A measured volume of Paraffin-free based solvent is drawn from the chemical tank 29 through a coupler 75 and transferred to the solvent regenerator 28 where it is heated to 60° C. The jacket heater 40 of the solvent regenerator and the vacuum pump 31 are energized. A normally closed control valve 42 is opened and liquid Paraffin is transferred from the Paraffin makeup vessel 27 to the reaction container 11 until a Paraffin level detector 62 inside the reaction container is triggered. At this time, the control valve 42 is closed, and the vacuum pump 31 is stopped. Control valves 43, 44, and 45 are opened and solvent is transferred from the solvent regenerator 28 to the reaction container 11. When the level detection switch 67 in the reaction container is triggered, the solvent pump 30 is stopped. At this point, all control valves are positioned to create the loop configuration described earlier. The process heater 39 and the solvent pump 30 are energized. The solvent and Paraffin are allowed to blend for about ten minutes into the final dissolving compound. The circuit is reconfigured to transfer the entire blended compound to the solvent regenerator 28. The reaction container 11 is evacuated. The system is now ready to process specimens.

A process for solvent recovery and regeneration is also described in U.S. Publication No. 2009/0298172 and illustrated in prior art FIG. 2. The objective is to recover, purify, and re-use extraction solvents by isolating and filtering cellular solutes from the dissolving compound for waste disposal. U.S. Publication No. 2009/0298172 also describes a technique for dissolving compound waste gas disposal.

U.S. Publication No. 2009/0298172 describes temperature and pressure preconditioning of the dissolving compound as follows.

The cellular solute extracting mixture is loaded into the chemical tank 29. A bottle coupler 75 provides a connection for solvent transfer and venting. Valves 46, 44 and 43, are open and the solvent pump 30 transfers mixture into the solvent regenerator 28. Valves 47 and 49 are opened to provide a path to the thermocatalytic oxidizer 37. Once the mixture is transferred from the chemical tank to the solvent regenerator, valves 46 and 47 close. The transfer is monitored by level control switches. Valve 45 is opened and the mixture is heated in the regenerator loop, using the process heater 39 and the regenerator jacket heater 40.

Vent gases are delivered to the thermocatalytic oxidizer 37 for oxidation to carbon dioxide and water as follows. Valve 50 is opened, the vacuum pump 31 is energized. Waste gases are delivered to the oxidizer. Once the inline thermal conductivity detector detects room conditions, valve 49 and 50 close and the vacuum pump is turned off. The mixture is heated to the desired temperature and pressure, e.g. 60° C. and about 0.8 bars (12 psig). It should be noted that the solvent regenerator operating conditions are flexible, and that it can heated from 20 to 100° C. and pressurized to from 1 to about 3.5 At. In addition, the variable flow and pressure solvent pump will operate equally over a wide range of temperatures and pressures. A flow orifice may be placed on the discharge to insure proper pump lubrication. Also, it is worth noting that the Paraffin present in the solvent also provides lubricating properties for pumps and valves.

SUMMARY

A single dissolving compound forms plural azeotropes, which can be azeotropically vaporized off at various stages of the treatment process, thus maintaining predictable concentrations of the chemicals present. The treatment process can be performed in the absence of formalin or related compounds which can interfere with the preservation of genetic material.

According to one aspect, a process for preserving a specimen includes using a dissolving compound that can be converted to a gas without damaging the specimen. The dissolving compound that extracts specimens-supplied water can be azeotropically converted to a gas at a plural of temperatures and pressures. The dissolving compound can be removed from the specimen by converting dissolving compound components to a gas by component vaporization and/or by forming one or more azeotropes at a plural of temperature and pressures. The dissolving compound can be converted to a gas and impregnates the specimen with support medium.

According to another aspect, a process for preserving a specimen includes using a dissolving compound that can form a plural number of azeotropes, at least one azeotrope being formed between one or more components of the dissolving compound and specimen-supplied water, and at least one azeotrope being formed between different components of the dissolving compound; successively and azeotropically vaporizing off formed azeotropes; and impregnating the specimen with a support medium.

Embodiments of this and other aspects may include one or more of the following.

The successively and azeotropically vaporizing off the azeotropes occurs at successively increasing boiling point temperatures. The azeotropes form at successively higher temperatures.

The dissolving compound comprises methanol, tetrahydrofuran, toluene, and zinc acetate. The azeotropes formed comprise tetrahydrofuran-methanol, toluene-methanol, tetrahydrofuran-water, and toluene-water.

According to another aspect, a process for preserving a specimen includes dissolving and removing cellular solutes in the specimen using a dissolving compound; partially removing the dissolving compound by forming two or more azeotropes with component agents of the dissolving compound, and azeotropically vaporizing off the two or more azeotropes; and replacing the solutes with an impregnated support medium.

Embodiments of this and other aspects may include one or more of the following.

The process is performed in a continuous sequence of steps within a single vessel. The process is performed in the absence of formalin. The impregnated support medium includes paraffin. The impregnated tissue support medium is selected from paraffin, plastic polymers, polyvinyl alcohol, polyethylene glycols, waxes, cellulose derivatives, agars, gels, and sugars.

According to another aspect, a process for preserving a specimen includes removing from the specimen cellular solutes that interfere with preservation and replacing the removed solutes with an impregnated support medium. The removing includes extracting an amount of water supplied by the specimen. The extracting includes dissolving the solutes including the amount of water using a dissolving compound; forming an azeotropic water-containing mixture of the amount of water and a component of the dissolving compound; azteotropically vaporizing off an amount of the azeotropic water-containing mixture. The process includes forming a second azeotropic mixture of at least two components of the dissolving compound; and azteotropically vaporizing off an amount of the second azeotropic mixture.

Embodiments of this and other aspects may include one or more of the following.

The removing includes clearing an amount of the dissolving compound from the specimen. The clearing includes forming an azeotropic fixitive-containing mixture of an amount of a fixitive agent component present in the dissolving compound and another component in the dissolving compound; and azteotropically vaporizing off an amount of the azeotropic fixitive-containing mixture.

The removing includes clearing an amount of the dissolving compound from the tissue. The clearing includes forming an azeotropic dehydrant-containing mixture of an amount of a dehydrant agent component present in the dissolving compound and another component in the dissolving compound; and azteotropically vaporizing off an amount of the azeotropic dehydrant-containing mixture.

The impregnated support medium includes paraffin. The impregnated support medium is selected from paraffin, plastic polymers, polyvinyl alcohol, polyethylene glycols, waxes, cellulose derivatives, agars, gels, and sugars.

The dissolving compound includes a single component or groups of components that is removed by vaporization from the specimen without damage to the specimen. The dissolving compound includes a single component or groups of components that release formaldehyde from the specimen and convert it to a monomeric gas. The dissolving compound includes a support medium component.

The dissolving compound includes a fixative component, a dehydrant component, and a clearing agent component. The dissolving compound includes a cation as a cellular anti-rupturing agent. The cation cellular anti-rupturing agent includes a compound selected from the group of zinc acetate, iron acetate, magnesium acetate, zinc citrate, iron citrate, and zinc malate. The fixative component is selected from the group of formalin, glacial acetic acid, zinc chloride or zinc sulfate, chromic acid, ethanol, methanol, acetone, mercuric chloride, picric acid, and potassium dichromate. The dehydrant component is selected from the group of alcohols, isopropyl alcohol, ethanol, denatured alcohols, butanols, ethers, ketones, dioxane, and acetone. The clearing agent component is selected from the group of xylene, toluene, benzene, acetone, butanols, dioxane, methyl salicylate, cedarwood oil, hexane, heptane, octane, and decane. The dielectric constant of the clearing agent component is between 2.0 and 10. The dissolving compound includes a mixture of between about 0 and 30% by weight alcohol, between about 45 and 99% by weight ether, and between about 0 and 20% by weight hydrocarbon.

The process includes prefixing the specimen using an amount of fixative including a mixture of between about 20 and 50% by weight methanol, and between about 20 and 50% by weight ethanol. The mixture is saturated with anhydrous ammonia. The mixture has a pH maintained between about 5.0 and 5.4 through the application of an effective amount of glacial acetic acid. The mixture includes an amount of vanadyl-ribonucleoside complex or RNAlater® as a nucleic acid preservative.

The process includes prefixing the specimen using an amount of fixative including a mixture of between about 80 and 98% by weight methanol, between about 1 and 20% by weight acetonitrile, and between about 1 and 5% by weight EDTA. The mixture has a pH maintained between about 5.0 and 5.4 through the application of an effective amount of glacial acetic acid.

According to another aspect, a dissolving compound includes one or more pre-polymers that polymerize to form a support medium. The dissolving compound is convertable to gas without damaging one or more specimens at a plurality of temperatures and pressure.

Embodiments of this and other aspect may include one or more of the following.

The dissolving compound includes volatile components that are convertible to gas at a pressure greater than 10 torr and a temperature of no more than about 150° C. The support medium is UV curable. The dissolving compound is a pre-fixative. The dissolving compound contains one or more photo-initiators. The dissolving compound contains 2-hydroxyethyl methacrylate and triethylene glycol dimethacrylate. The dissolving compound contains urethane acrylate, ethoxylated trimethylolpropane triacrylate, methacrylic acid and 2-hydroxyethyl methacrylate. The dissolving compound contains one or more plasticizer, for example, phthalates, benzoates, adipates or trimelliates.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
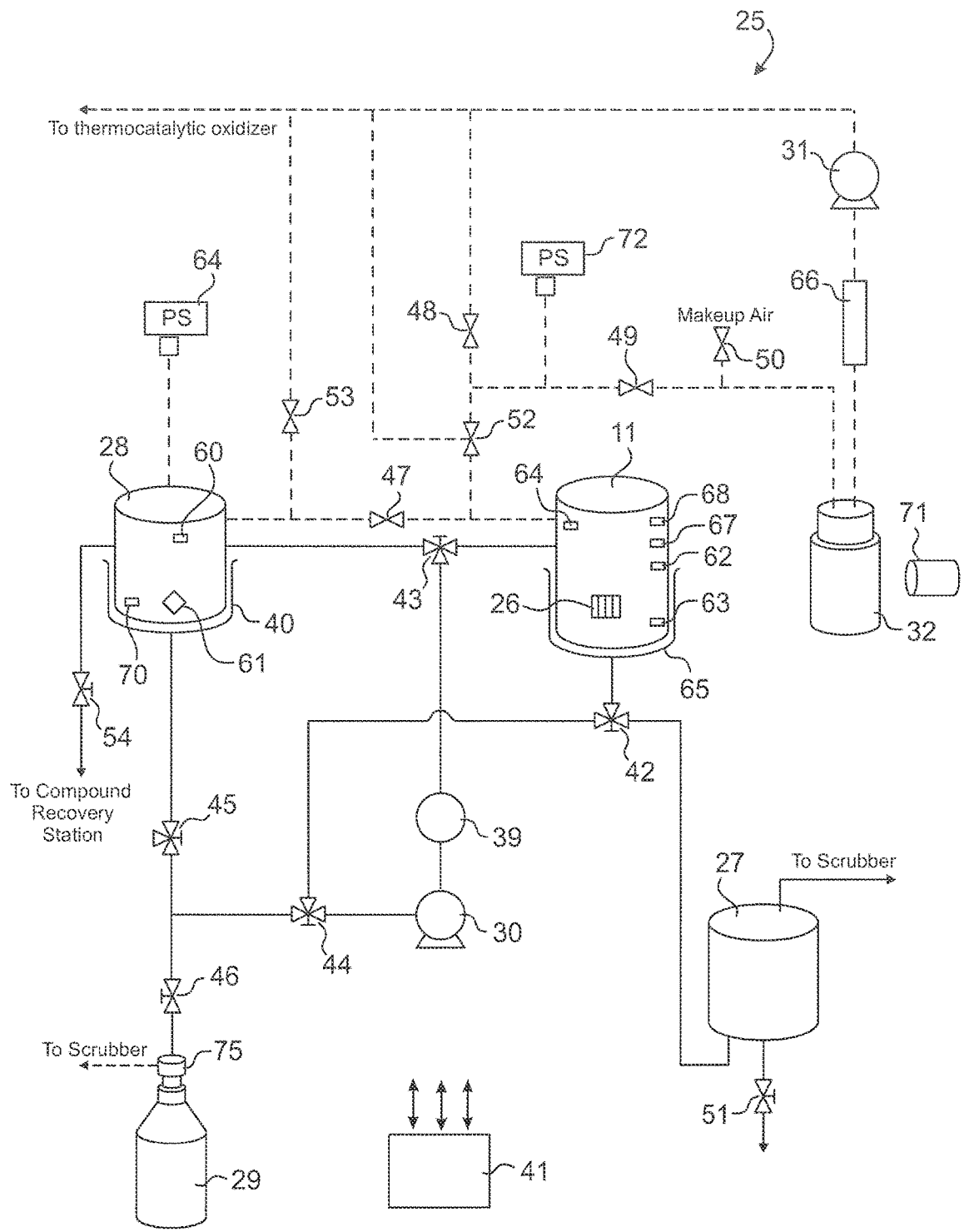
FIG. 1 is a prior art diagrammatical schematic illustration of an apparatus for preserving a specimen.
Figure 2:
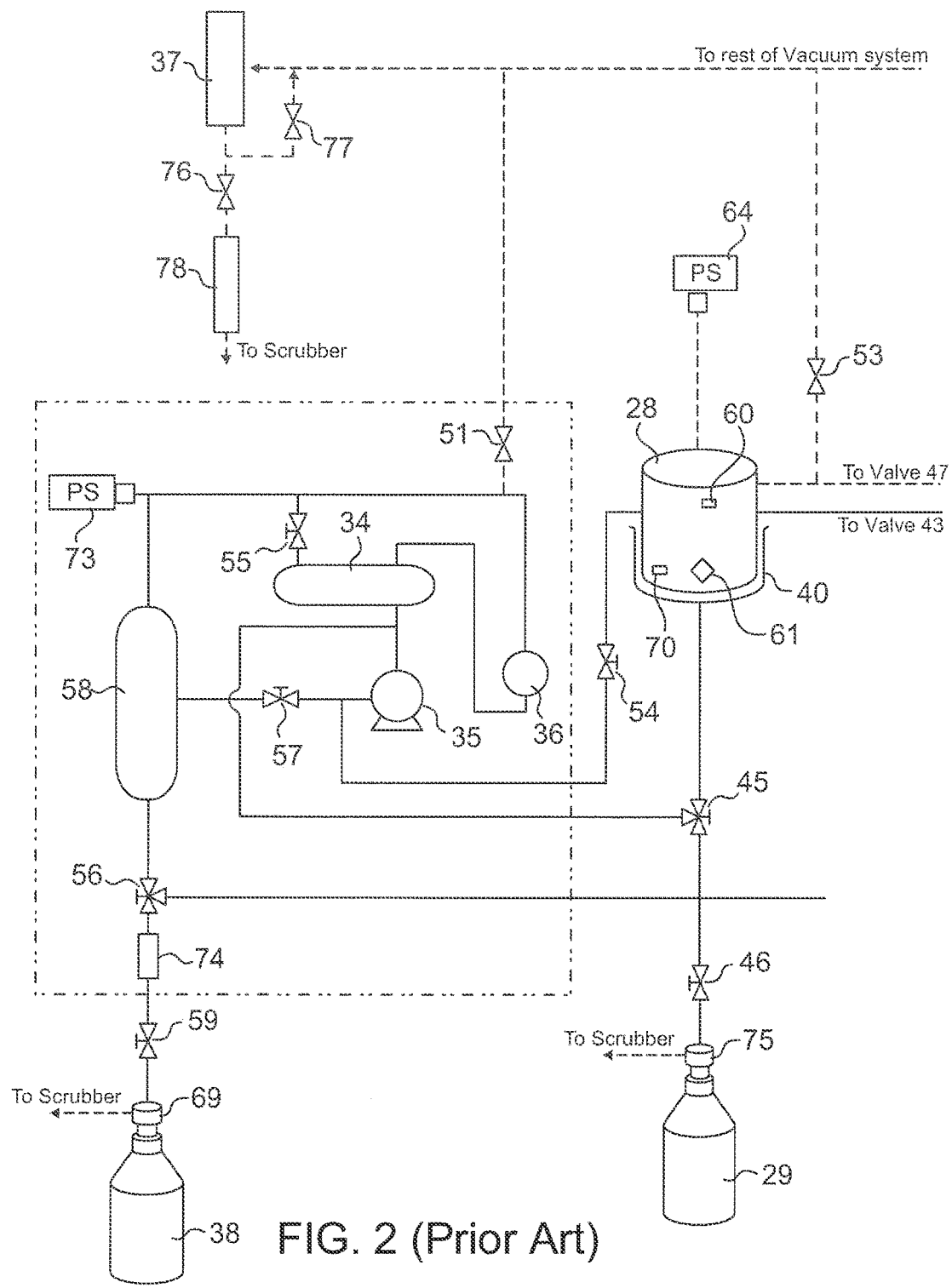
FIG. 2 is a diagrammatical schematic illustration of the solvent regeneration portion of the apparatus.
Figure 3:
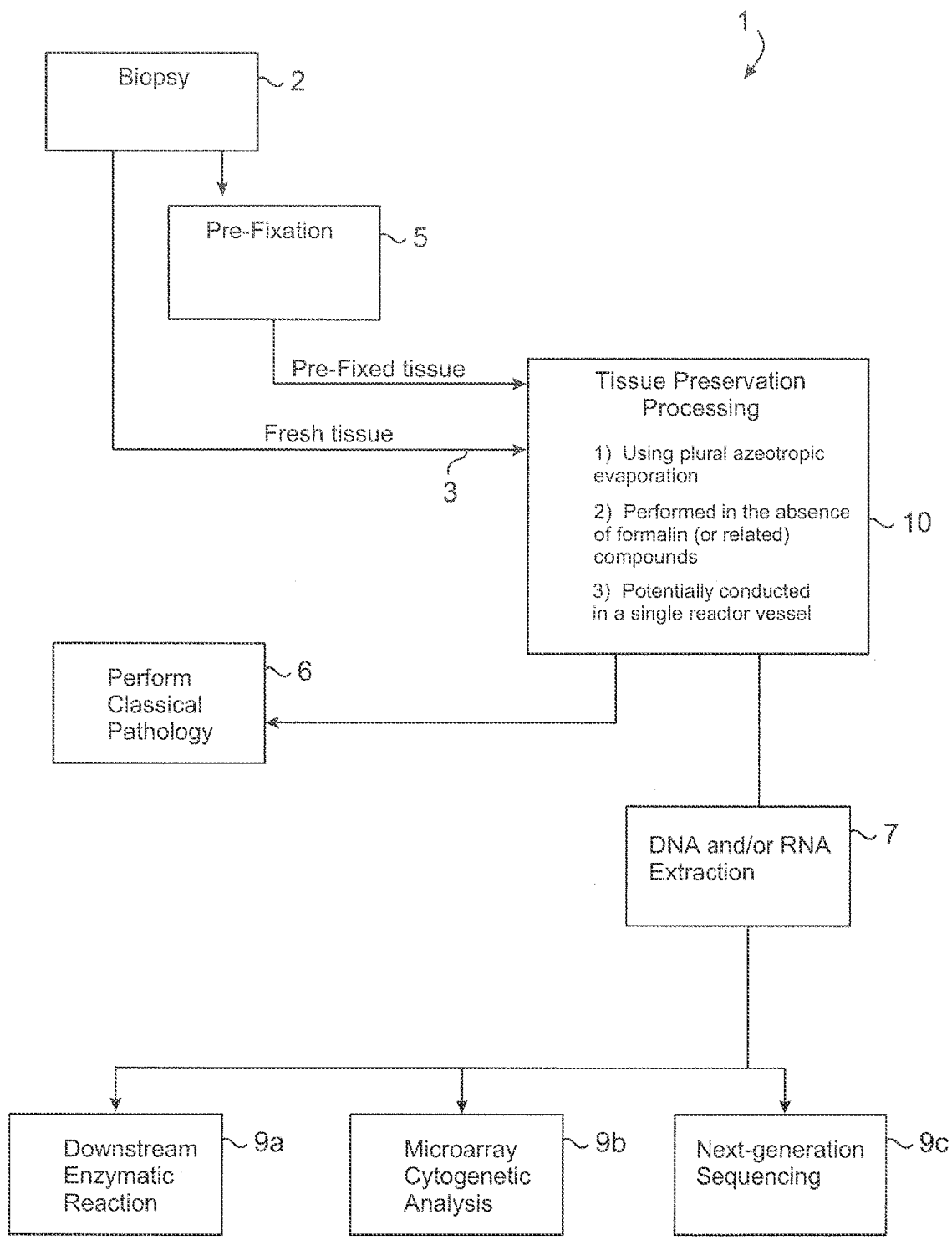
FIG. 3 is a flow diagram of tissue histology according to an exemplary embodiment of the invention.

Referring to the drawings there is shown in FIG. 3 a flow diagram of tissue histology 1. First a biopsy 2 is performed to obtain the tissue specimen to be preserved and analyzed. The fresh tissue specimen 3 can be sent directly to preservation processing 10. Alternately, the fresh specimen can undergo a pre-fixation process 5 before being sent to preservation processing. The histology process can also be performed on plant or vegetable matter.

After preservation 10, some or all of the preserved tissue specimen can undergo standard "classical" pathological analyses 6, and/or some or all of the preserved tissue specimen can undergo a DNA/RNA extraction process 7, where the extracted genetic material can be supplied to one or more genetic analysis processes including downstream enzymatic reaction analysis 9a, cytogenetic analysis using microarray technology 9b, and/or next generation sequencing 9c or molecular analysis.

In the prior art preservation process described above, two azeotropes are formed. One of the azeotropes, acetone-hexane, is formed with the dissolving compound. The other azeotrope (hexane-water) is not formed with the dissolving compound. In preservation process 10 two or more azeotropes are formed with the dissolving compound.

Figure 4:
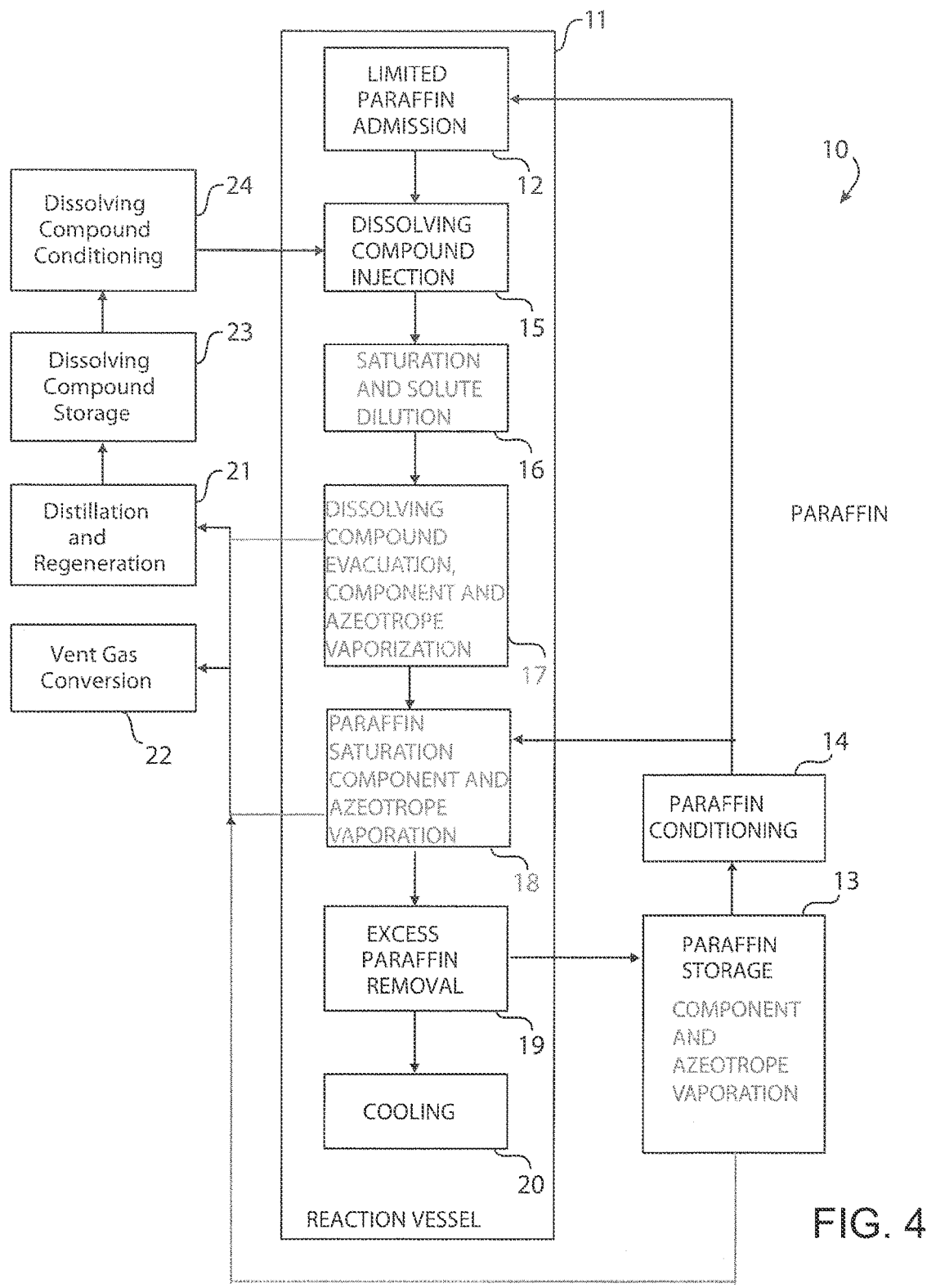
FIG. 4 is a flow diagram of a tissue preserving process according to an exemplary embodiment of the invention.

Referring to FIG. 4, the tissue specimen preserving process 10 includes, in a hermetically sealable, and pressure and temperature controllable reaction vessel or container 11 in which one or more tissue specimens are being held, admitting at 12 a limited volume, for example, about 200 ml of melted tissue support medium such as paraffin from a storage tank at 13. The paraffin has been preferably conditioned at 14 by raising its temperature slightly above its melting point, for example, 60° C., such that heated support medium in a liquid state is admitted into the container 11.

The limited paraffin admission at 12 mixes with subsequently introduced dissolving compound and acts to decrease the infiltration time into the specimens of further subsequently introduced paraffin.

A dissolving compound formulated to dissolve cellular solutes in the specimens is then introduced at 15 into the container 11. These cellular non-volatile solutes that are dissolved by the dissolving compound include lipids: glycerides, triacylglycerols, phospholipids, sphingolipids, fatty acids and cholesterol. Other extractable species include soluble vitamins, cellular waste products and a host of other biochemical molecules. There are two types of cellular water present in the specimens, bound and free water. Only free water is extracted by the dissolving compound. The components of the dissolving compound now mixed with the paraffin introduced at 12 penetrate the specimens at 16, with the dissolving compound diluting and extracting solutes while the specimen becomes saturated with the dissolving compound.

The solutes that are diluted and extracted from the specimens as well as excess dissolving compound that did not enter the specimens are evacuated from the container 11 in liquid form at 17 and returned to the regenerator at 21. Formaldehyde that may be present in the specimen from fixation is converted by the dissolving compound from bound formaldehyde to a monomeric gas free formaldehyde. During an evaporation cycle at 17, the monomeric gas trapped in the top region of the container 11 is pulled out through a vent at the top of the container 11 at 22.

To remove the residual dissolving compound present in the tissue, the pressure and temperature in the container 11 are controlled at 17 to vaporize the residual dissolving compound and form a plurality of azeotropes of the dissolving compound, as described further below. In particular, a vacuum is pulled to remove dissolving compound from the specimen through component evaporation and azeotrope formation. The temperature and pressure are controlled in an evaporation cycle to form a distinct azeotrope molecular species of cellular free water with components of the dissolving compound. Further azeotropes are also formed from components of the dissolving compound. All of the azeotrope gaseous species and the free formaldehyde are removed from container 11 through the vent at 22.

The paraffin from the dissolving compound/paraffin mixture that had been deposited in the specimen from the dissolving compound saturation of the specimen remains in the specimen. The container 11 is then flooded at 18 with about 5 liters of paraffin mixed with dissolving compound, which saturates the specimens. The dissolving compound mixed with the paraffin is an entrained amount absorbed by the paraffin, and the dissolving compound acts to decrease the viscosity and the infiltration time of the paraffin. The pressure in the container 11 is then reduced and the temperature controlled such that components of the dissolving compound are vaporized and azeotropes are produced at 18 in the same manner as described at 17. The gaseous species are again removed through the vent at 22. After removal at 19 of excess paraffin in liquid form from the container 11, the container is cooled at 20 allowing retrieval of the treated specimens.

The evacuated dissolving compound components carrying the removed solutes can be regenerated by distillation at 21 and by converting at 22 the waste gases into carbon dioxide and water through a thermocatalytic oxidizer. The recovered dissolving compound can then be stored at 23 and then pressure and temperature preconditioned at 24 prior to being used again in the container 11 such that heated and pressurized dissolving compound is introduced into the container 11 at 15.

Figure 9A:
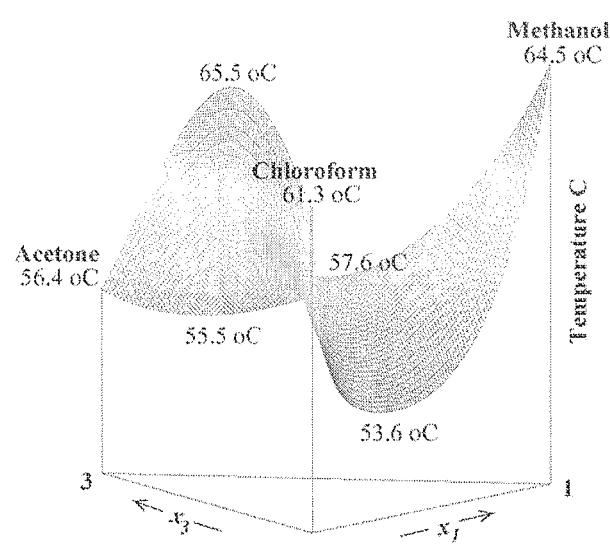
FIGS. 9A and 9B are graphs of azeotropic behavior of a ternary mixture used in specimen preservation.
Figure 9B:
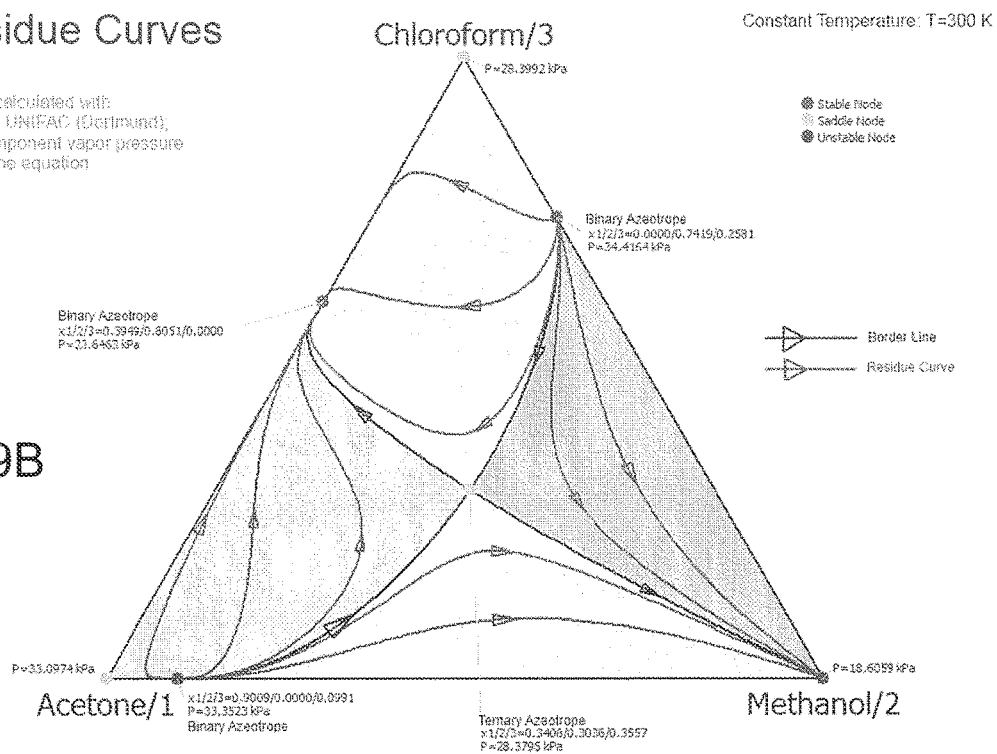

In steps 17 and 18, the pressure and temperature in the container is adjusted to successively azeotropically evaporate the dissolving compound components present in the specimens. For example, FIGS. 9A and 9B demonstrate the complex azeotropic behavior of a ternary dissolving compound mixture of methanol, acetone, and chloroform used in specimen preservation. The mixture forms three binary azeotropes and one ternary azeotrope at atmospheric pressure. A binary azeotrope of chloroform and methanol has a boiling point of 53.6° C.; a binary azeotrope of acetone and methanol has a boiling point of 55.5° C.; a binary azeotrope of acetone and chloroform has a boiling point of 65.5° C.; and a ternary azeotrope of methanol, acetone, and chloroform has a boiling point of 57.6° C. A general property of azeotropes is that a variation in pressure changes the boiling temperature and the composition of the mixture. The methanol and acetone act as the fixative, the acetone acts as the dehydrant, and the acetone and chloroform act as the clearing agent.

The three binary azeotropes and one ternary azeotrope together with the three pure components form a system having seven nodes which altogether form four distallation regions. Two nodes are stable (pure methanol and the binary azeotrope of chloroform and acetone), which both have the lowest vapor pressure (isothermal calculation) in the two regions they are part of. The other two binary azeotropes are unstable nodes. They have the highest vapor pressure in their regions. The other nodes are saddles (the ternary azeotrope, the pure acetone and the pure chloroform). The border lines in this system connect the ternary azeotrope (saddle) with the two stable nodes and the two unstable nodes. The residue curves are always moving away from an unstable node to a saddle but never reach a saddle because the residue curves then turn to a stable node.

As discussed further below, successive azeotropes are formed, for example, as the temperature is raised to 60.7° C., 63.5° C., and 64° C. Each azeotrope is vaporized off by using the diffusion pump 66 to reduce the pressure. Vacuum is applied until pressure equilibrium is achieved, for example, about 0.9 atmospheres to about 0.99 atmospheres (−27 to −29.91 inches Hg), depending upon the component being removed. Once equilibrium is reached, all volatile solvent molecules have been removed from the reaction container and specimens. After the first azeotrope is vaporized off, the temperature is raised to form the next azeotrope, and so on. The process is allowed to continue for each additional components for up to 10 to 30 minutes depending upon the total mass of specimens. The rise in temperature and the evacuation of gasses through the vent at 22 occur at the same time.

Dissolving Compound

The dissolving compound can be selected from various mixtures of component chemicals for use in the above described tissue preservation process and associated apparatus. The chemicals or mixtures thereof can act as one or more functional components of the dissolving compound. These functional components include a fixation agent component, a dehydration agent component, and a clearing agent component. Optionally, the dissolving compound can be blended with an impregnation agent such as paraffin. Optionally, dissolving compound can also include a cation (examples include but are not limited to zinc acetate, iron acetate, magnesium acetate, zinc citrate, iron citrate, and zinc malate) as a cellular anti-rupturing agent.

Significantly, the dissolving compound is a mixture of component agents that form one or more azeotropes during different stages in the process, and thus the dissolving compound and its components can be removed without damaging the specimen. Azeotropes can be used to extract cellular water from the tissue, remove components of the dissolving compound from the tissue, and deposit dissolved paraffin or other media into the tissue specimen. Therefore, each step in the tissue processing, namely fixation, dehydration, clearing and infiltration, can be accomplished using the supplied dissolving compound. In this way, a single dissolving compound can be used to perform all the steps necessary for tissue preservation.

Further, it shall be understood that, if desired, the dissolving compound can be selected to perform a fewer number of the preservative functions. So, for example, a dissolving compound can be selected to fix, dehydrate and clear only, or selected to dehydrate and clear only. Accomplishing the process in whole or in part depends upon the chemicals employed and specimen type.

Further, the dissolving compound can contain one or more components that form one or more azeotropes in the presence of paraffin or other support media used in the infiltration step. Support media other than paraffin can include but are not limited to polymeric compounds, like polyethylene glycols, waxes such as carbowax, resinous or acrylics polymers, cellulose derivatives, agars, gels, and sugars. The support media can be composed of monomeric, cross linking agents and/or copolymers that infiltrated the specimen and cure, to produce a polymeric support medium. These compounds are added to the prefixative reagent and/or the dissolving compound and may contain photoinitiators to accelerate the polymerization reaction. Examples of pre-polymer compounds include, but are not limited to, Urethane acrylate, methacrylic acid, 2-hydroxyethyl methacrylate, ethoxylated trimethylolpropane triacetate, triethylene glycol dimethacrylate, and hexadecyl methacrylate. The paraffin or other support media can vary between 0 and 20 percent by weight of the combination of dissolving compound and support media.

In general, common chemical compounds that can be used to form the azeotropically removed dissolving compound used in tissue preservation include but are not limited to alcohols, organic acids, alky halides, esters, ketones, aldehydes, ethers, aromatics, solvents, oxygenates and hydrocarbon blends.

During the fixation stages, the removal of dissolving compound components is not yet required. In other words, fixation can occur prior to the removal of any of the components of the dissolving compound. In addition fixation can also occur during removal of the dissolving compound, where the fixative is vaporized with one or more components of the dissolving compound.

During dehydration stages, water and hydrated solutes can be extracted from tissue using liquid-liquid extraction using more than one reagent of similar chemical composition. Components of the dissolving compound form hydration spheres with free water, creating a compound that can be vaporized at temperatures that will not damage the tissue specimen. Thus, when using a single reagent, the final amount of water and residual dissolving compound is removed by azeotrope formation. In tissue preservation processing, azeotropes used to remove water from tissue and the dissolving compound are those that have an azeotropic boiling point of 150° C. or less, more preferably 115° C. or less, and most preferably less than 100° C. so that the tissue is not damaged by the temperature of boiling.

Components that form azeotropes with water include, but are not limited to ethanol, n-propanol, isopropanol, n-butanol, sec-butanol, iso-butanol, tert-butanol, ally alcohols, formic acid, propionic acid, butyric acid, iso-butyric acid, ethylene chloride, propylene chloride, chloroform, carbon tetrachloride, methyl chloride, ethyl acetate, methyl acetate, n-propyl acetate, ethyl nitrate, methyl ethyl ketone, pyridine, benzene, toluene, cyclohexane, hexane, heptane, octane, m-xylene, p-xylene, ethylbenezene, diethyl etther, tetrahydrofuran, anisole, acetonitrile, chloral, and hydrazine.

Azeotropes can also be used during clearing stages to remove components of the dissolving compound, such as the fixative, the dehydrants, and clearing agents themselves or any combination thereof. The dissolving compound can be composed of one or more azeotropes containing a clearing agent. Examples of clearing agents include but are not limited to methyl salicylate, cedar wood oil xylene, toluene, benzene, aromatic solvent 150, terpineol, carbon tetrachloride, chloroform, dioxane, celloslove, tetrahydrofuran, and butanols.

Finally, the dissolving compound is designed to be vaporized in a manner that results in the preservation of tissue specimens without damage to the specimen, and the dissolving compound is used to deposit support medium to the tissue specimen through vaporization.

During tissue processing a small amount of dissolving compound is trapped in the lines from vessel 11 and valve 42, and is transferred into the paraffin storage at 13. The dissolving compound is designed to be entrained within the paraffin. This modifies the paraffin so that its viscosity is reduced for faster infiltration. The dissolving compound present in the paraffin storage vessel is regulated so that the amount of entrained dissolving compound is approximately constant. Thus, during paraffin infiltration and storage, water present in the paraffin can be removed from the paraffin by azeotrope formation at 13.

Prefixing

Fresh tissue can be prefixed, that is, undergo a fixation process prior to being processed by the dissolving compound. For example, the biopsied tissue can be first exposed to a solution of ten to twenty percent formalin. Exposure time may vary from 2 minutes to 48 hours. After this exposure the tissue is processed in a tissue processor using a dissolving compound which forms one or more azeotropes, as described above.

Prefixation can also be done using a fixative which is intended to preserve genetic material and avoids the use of formalin. For example, a solution of 20 to 50 percent by weight ethanol and 20 to 50 percent by weight methanol is bubbled with anhydrous ammonia until saturated. The pH of this saturated solution is maintained between 5.4 and 5.0 using glacial acetic acid. Vanadyl-ribonucleoside complex or RNAlater brand reagent commercially available from Qiagen of Hilden, Germany can be added to further preserve the nucleic acids. The tissue specimens can be treated for up to 12 hours, to preserve RNA. Thereafter, the prefixed tissue can be processed using the dissolving compound, as described above. The processed tissue specimens can be stored for 5 years, without derogation of its DNA. These tissue specimens may be extracted and sequenced or analyzed for nucleic acids using microarray-based testing (cytogenic array) as well as conventional pathology testing.

In an alternate example of prefixation in order to preserve genetic material a solution of methanol 70-98 percent by weight and acetonitrile 1-20 percent by weight, and EDTA 1-5 percent by weight are blended, and glacial acetic acid is added to maintain a pH between 5.4 and 5.0. The tissue specimens may be treated for no more than 24 hours to preserve RNA, and then processed using an azeotropically removed dissolving compound tissue process, as described above. The processed tissue specimens can be stored for up to 5 years and analyzed for nucleic acids using microarray-based clinical testing as well as traditional pathology testing.

Specimens Protocol for Processing Using Dissolving Compound

Protocol 1:

Specimen Prefixing Formaldehyde Free or Formalin Fixed Specimens

Ensure that the grossed sections are thin, preferably no more than 3 mm thick.

Place specimen in fixative as soon as possible after the blood supply has been interrupted.

Open specimens wherever possible. Gastrointestinal specimens should be opened, pinned to a cork or paraffin wax board and placed in fixative. Uterus specimens should also be opened and placed in fixative. Lungs can be inflated with fixative by gravity flow.

Slice specimens, such as spleen, breast, kidney, any organ resection, or large tumor into slices and place in fixative.

Bisect lymph nodes when appropriate and place in fixative.

Place fixative container for holding cassettes on stir plates, and provide agitation to enhance the fixation and penetration process.

Use only fresh fixative solution. Ensure that the fixative volume is 15 to 20 times the tissue volume.

Well-grossed sections of routine tissue should be fixed at least 8 to 12 hours to ensure at least adequate fixation, but no more than 24 hours.

For processing of fresh tissue specimens, where the specimens meet the definition of needle biopsies (up to 1 mm thick), the protocol for Prefixing Formaldehyde Free above is followed for transport to the laboratory, omitting the last step of fixing for at least 8 to 12 hours.

Stain Protocol: after the specimens are processed as described above with reference to FIG. 4, and embedded in a paraffin block, cut and placed on a slide, Hematoxylin and Eosin Y are used to stain the specimens on the slide. Steps 1-22 of the staining process are set out in the table below.

| 1 | Xylene | 3 min |
|---|---|---|
| 2 | Xylene | 3 min |
| 3 | Xylene | 3 min |
| 4 | 100% Alcohol | 1 min |
| 5 | 100% Alcohol | 1 min |
| 6 | 100% Alcohol | 1 min |
| 7 | 80% Alcohol | 30 sec |
| 8 | Wash in H2O | 1 min |
| 9 | Hematoxylin | 2 min |
| 10 | Wash in H2O | 1 min |
| 11 | Differentiate | 30 sec |
| 12 | Wash in H2O | 1 min |
| 13 | Bluing agent | 30 sec |
| 14 | Wash in H2O | 1 min |
| 15 | 80% Alcohol | |
| 16 | Eosin Y - Alcoholic | 20 sec |
| 17 | 100% Alcohol | 1 min |
| 18 | 100% Alcohol | 1 min |
| 19 | 100% Alcohol | 1 min |
| 20 | Xylene | 1 min |
| 21 | Xylene | 1 min |
| 22 | Xylene | 1 min |

Example 1

A dissolving compound is selected containing an alcohol, ether, and an aromatic hydrocarbon. The concentration of the components may vary, but typically the alcohol is between 0 and 30 percent by weight, the ether between 45 and 99 percent by weight and the aromatic between 0 and 20 percent by weight. The alcohol can act as a fixative component. The ether can act as a dehydrant and clearing component. The aromatic can act as a fixative, dehydrant and clearing component.

The tissue can be exposed to the dissolving compound for a specified time (10-120 minutes) under a specific pressure (50-350 kPa) and temperature (25-99° C.) in order to completely saturate the specimen with dissolving compound, and allow liquid extraction of the cellular solutes. Liquid dissolving compound containing cellular solutes is drained from the reactor. Thereafter, using temperature and pressure variations, the remaining dissolving compound is removed from the tissue by the successive formation and vaporization of azeotropes in a proper order. Thereafter, the tissue is suitable for pathological and cytogenetic examination.

Using the alcohol/ether/aromatic dissolving compound, the first azeotrope that forms is fixative based and is removed by formation of an ether-alcohol azeotrope. Thus, at this point, the dehydrant and/or clearing agent can be used to remove the balance of the fixative by vaporizing the developing azeotrope.

Next, water remaining in the tissue reacts with the remaining ether dehydrant to form an ether-water azeotrope which can be removed by azeotropic vaporization. At this stage, by removing most of the water, the tissue's polarity has changed.

Next, the clearing agent can be removed by azeotrope formation and its azeotropic vaporization.

The rate and amount of removal of these azeotropes is controlled by varying the pressure and/or temperature of the reactor. Specifically, the pressure varies from 350 kPa to 25 kPa, more specifically between 175 kPa and 60 kPa and even more specifically between 100 kPa and 45 kPa. Specifically, the temperature varies from about 30° C. to about 150° C., more specifically the temperature varies from about 30° C. to about 100° C.

This example shows that in forming the dissolving compound, one or more alcohols can be blended with a low molecular weight oxygenate and/or hydrocarbon that extract cellular solutes that interfere with infiltration, and removal of the dissolving compound is achieved by the formation of one or more azeotropes.

This example further shows that an azeotrope mixture can be used to fix and/or dehydrate the tissue being preserved.

Further, this example shows that the clearing of the tissue can be accomplish by a low boiling point component, where the boiling point can be less than 150° C. Examples of chemicals useful as a low boiling point clearing agent component include, but are not limited to C4 through C15 hydrocarbons, branches chain alkyl alcohols, C4 through C12 oxygenates, chlorinated hydrocarbons, brominated hydrocarbons, and other aromatic hydrocarbon solvents having a boiling point of 150° C. or less.

Example 2

A dissolving compound is selected containing 20 percent by weight methanol and 80 percent by weight tert-butanol. The dissolving compound is charged to the container 11 containing tissue specimens at 40° C. The specimen is exposed to the dissolving compound for 30 minutes and the dissolving compound is drained from the reactor. The reactor temperature is slowly elevated to 65° C. while the pressure is varied between 50 and 200 kPa. The residual methanol is converted to a gas and is vented during the pressure cycle. In this example the methanol is removed as a zeotrope. After a period of time the reactor temperature is raised to 80° C. and the tert-butanol slowly forms an azeotrope with residual water present in the tissue. During the temperature change and at the isotherm of 80° C., the reactor pressure is varied between 50 and 200 kPa. The azeotrope is removed from the reactor using the vent.

A solution containing Carbowax as the support medium is then charged to the reactor for impregnating the tissue. Pressure variation (for example, between 50 and 200 kPa) is again used to vaporize the residual tert-butanol/water azeotrope. The reactor temperature is dropped to 68° C., while the pressure variation continues, and the specimens are exposed to the carbowax medium for an additional 30 minutes.

Example 3

A dissolving compound is selected to include the chemicals shown in Table 3.1 below.

TABLE 3.1

Selected dissolving compound

| Component | Relative Weight Percent |
|---|---|
| Methanol | 15.2 |
| Tetahydrofuran (THF) | 79.0 |
| Toluene | 5.4 |
| Zinc acetate | 0.4 |

Tissue specimens of the type and volume shown in Table 3.2 were loaded into the container 11.

TABLE 3.2

Specimen type and volume

| Tissue | Dimensions (mm) |
|---|---|
| Intestine | 15 × 10 × 5 |
| Heart | 25 × 15 × 6 |
| Kidney | 30 × 25 × 5 |
| Breast | 30 × 25 × 6 |
| Liver | 20 × 15 × 5 |
| Uterus | 20 × 25 × 6 |

Tissue Processing: The dissolving compound described in Table 3.1 is stored at a temperature of 40° C. The heated dissolving compound is then transferred to the container 11 containing tissue specimens listed in Table 3.2. The reaction container's conditions are next equilibrated to 45° C., with a reactor flow rate of 4.0 l/min. Specimens are processed in the dissolving compound for 70 minutes.

During this processing time, zinc acetate is converted to a zinc-plasma-membrane chelate compound, and all tissue specimens become super saturated with dissolving compound. The zinc chelate helps provide increased cellular membrane integrity to limit tissue cell rupturing. The reactor container skin temperature is increased to 60° C., and the dissolving compound is returned to the storage vessel. Liquid paraffin at 59-72° C. is then added to the reactor container. Residual dissolving compound within the reactor container blends with the paraffin. The temperature of the solvent-paraffin blend is slowly increased to 68° C. and the pressure is varied between 50 and 200 kPa.

As the temperature of the dissolving compound/paraffin blend increases, four azeotropes are formed (Table 3.3). The dissolving compound and water and their azeotropes are removed from the reactor during the pressure variation and the gas is vented.

TABLE 3.3

Example of azeotropes that form during specimen processing. Table shows relative boiling points corrected to atmospheric pressure for reference only.

| Azeotrope Component 1 | Azeotrope Component 2 | Relative Boiling point of Azeotrope at atmosphere conditions (C °) |
|---|---|---|
| Tetrahydrofuran (THF) | Methanol | 60.7 |
| Toluene | Methanol | 63.8 |
| Tetrahydrofuran | Water | 65 |
| Toluene | Water | 84.1 |

It is important to note that the formation of successive azeotropes allows for the removal of all the dissolving compound components and all the cellular solutes being removed from the tissue at a temperature that is below their normal boiling point. For example, water boils at 100° C. without azeotrope formation, and toluene boils at about 110° C. A temperature of 100° C. would damage and destroy the tissue specimens, rendering them unsuitable for diagnosis. In addition, the presence of the selected dissolving compound results in a decrease in paraffin viscosity, thus increasing paraffin penetration, and resulting in ideal processing for large tissue specimens.

Figure 5:
FIG. 5 shows an H&E stained Uterus specimen processed using the azeotropically removed dissolving compound of Example 3.

FIG. 5 shows an H&E stained Uterus specimen processed using the azeotropically removed dissolving compound components listed in Table 3.1. The results show excellent tissue preservation. Further, in this way, tissue processing using plural and successive azeotrope formation results in a faster tissue preservation method when compared to conventional FFPE (Formalin Fixed Paraffin Embedded) methods.

Figure 6:
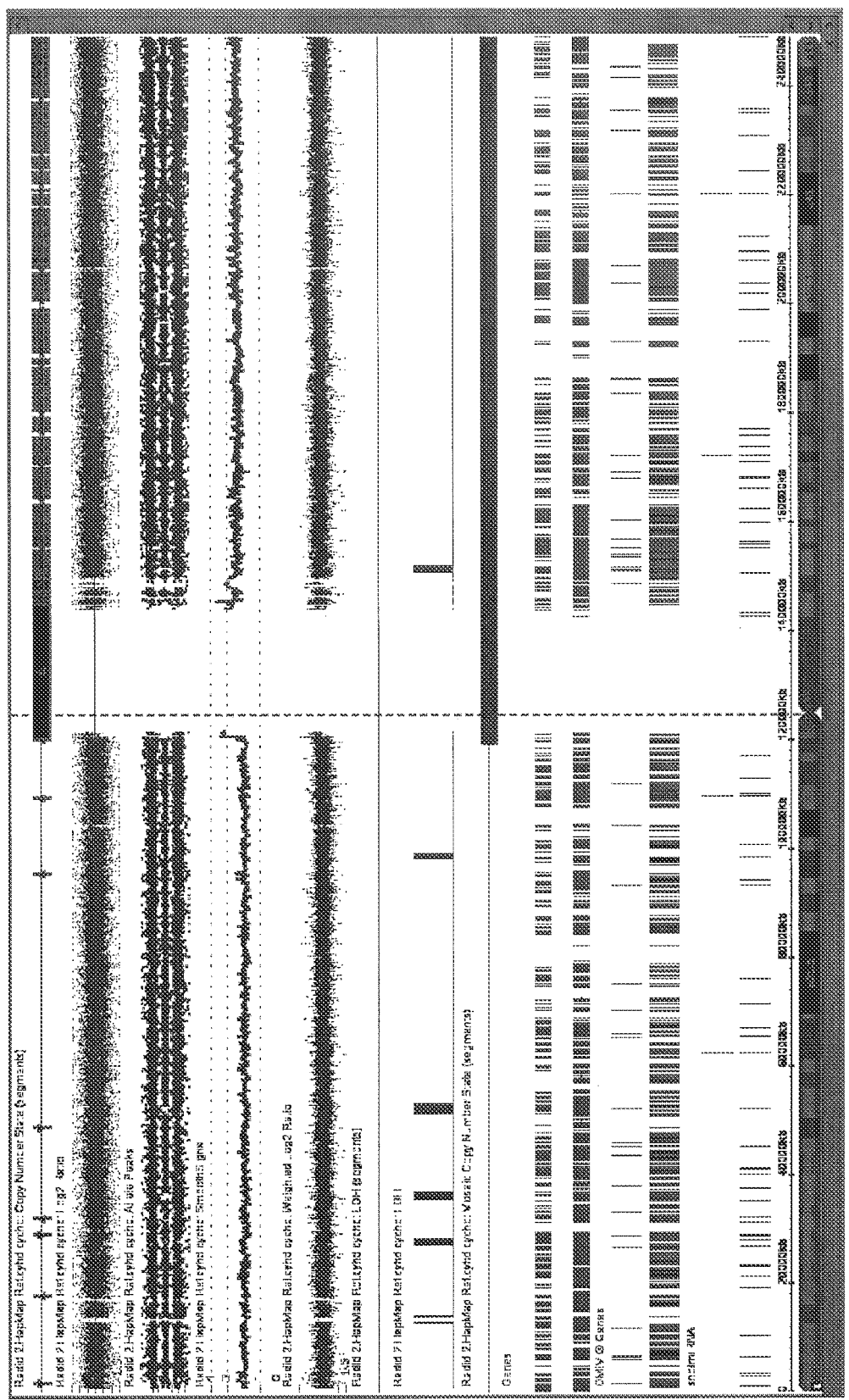
FIG. 6 is a CytoScan brand analysis output for a uterus specimen after processing employing the azeotropically removed dissolving compound of Example 3.

FIG. 6 shows a CytoScan brand analysis of uterus specimen after processing employing an azeotrope dissolving compound listed in Table 3.1 using GeneChip Scanner 3000 brand analysis equipment. The CytoScan analysis and GeneChip Scanner 3000 equipment are commercially available from Affymetrix of Santa Clara, Calif.

Example 3b

Specimens whose volume ranges from 1 $mm^3$ to 5000 $mm^3$ are placed in the reactor container 11. The reactor is sealed and a dissolving compound containing 185 grams of methanol, 960 grams of tetrahydrofuran, 250-400 ppm of 3,5-di-tert-butyl-4-hydroxytoluene (BHT), 66 grams of toluene and 5 grams of zinc acetate are charged into the reactor container at between 25° C. and 40° C. The dissolving compound is circulated at a variable rate between 1 and 10 liters per minute and heated to about 45° C. for a period of 70 minutes. The dissolving compound generates an internal reactor pressure between 130 and 165 kPa. During this time, there is mass transfer of the cellular solutes that interfere with tissue preservation from the tissue to the bulk phase of the dissolving compound. As part of the process the tissue is fixed, dehydrated, and cleared by the dissolving compound. Cellular components that cause autolysis, for example enzymes, are deactivated. In addition, there are substantial molecular configurational changes that render the component, for example, nucleic acids, DNA, RNAs, proteins, and carbohydrates, inactive. There is a polarity change in the tissue from polar to non-polar as more of the tissue interferences are removed.

At about 70 minutes liquid dissolving compound is drained from the reactor container. The reactor container walls are then heated from 45 to 68° C., and a slight vacuum of between 100 and 45 kPa is applied to the reactor. This generates the first azeotrope, namely a THF-methanol compound having a boiling point at about 60° C.

It is important to note that the azeotrope boiling point temperature is given at atmospheric conditions, 760 Torr, for reference only. The true azeotrope boiling point would be less than 60° C. at 60 kPa.

The azeotropic vaporization removal of the THF-methanol azeotrope decreases the methanol concentration within the tissue. The remaining methanol is removed by the second azeotrope, namely a toluene-methanol compound having a boiling point at about 63° C. As this process continues the polar methanol is removed and the tissue becomes non-polar and saturated with THF and toluene.

At about this point, paraffin containing a small amount of dissolving compound is charged to the reactor. The reactor pressure is reduced to about 60 kPa for about 1 to 3 minutes, and then pressure is applied between 100-210 kPa, for about 90 seconds. Any methanol present in the paraffin-dissolving compound is removing by azeotrope formation. The viscosity of the paraffin is also reduced by the presence of the dissolving compound, improving infiltration of the paraffin into the tissue.

The next azeotrope to form is THF-water. Any residual free water present in the tissue is thus removed by azeotropic boiling of the THF-water azeotrope at about 65° C. Toluene and THF tend to clear or brighten the tissue, freeing it from cloudiness, muddiness, and blemishes, resulting in a more transparent, and non turbid tissue.

The final azeotrope to form is toluene-water at about 68° C. and 60 kPa. Gases formed in the reactor are removed through the vent as the pressure is varied from about 50 to 210 kPa. A mixture of dissolving compound and paraffin floods the reactor, the reactor pressure is varied from about 50 kPa to 210 kPa, the dissolving compound paraffin mixture is heated from 50 to about 100° C., and gases formed are vented. The processing time varies from 30 minutes to about 4 hours and is dependent upon specimen volume.

At the end of this process specimens can be stored in liquid paraffin for about 30 seconds to about 100 hours, upon which excess paraffin is removed from the reactor, and samples are cooled to room temperature, and are suitable for embedding and microtome cutting. This tissue is then stained using conventional IHC or FISH stains. The remaining paraffin-loaded tissue blocks can then be stored for up to thirty years.

Example 3c

A dissolving compound is selected containing 79.1 percent by weight THF, 15.2 percent by weight methanol, 4.9 percent by weight 2-hydroxethyl methacrylate, 0.5 percent by weight triethylene glycol dimethacrylate, and 0.2 percent by weight of jayflex DUP and the dissolving compound is preheated to 50° C. The dissolving compound is charged to container 11 containing specimens and the specimens are exposed to the dissolving compound for 15 minutes. During that time the polymer precursor mixture infiltrates the specimens. The liquid dissolving compound is transferred from container 11 to container 28. The temperature of container 11 is elevated to 60° C. while the pressure is varied between 50 and 210 kPa. Volatile components and residual cellular water are removed from container 11 as gas through the vent. The pre-polymer infiltrated specimen is extracted from the container 11 and cured via UV light. The processed specimen is directly cut using a microtome followed by staining. The results show excellent tissue preservation.

Example 4

A dissolving compound is selected to include the chemicals shown in Table 4.1 below.

TABLE 4.1

Selected dissolving compound

| Component | Relative Weight Percent |
|---|---|
| Methanol | 24 |
| Ethanol | 14.6 |
| Hexane | 61.0 |
| Lubricity additive | 0.4 |

This dissolving compound is selected to extract tissue solutes that interfere with polymer or wax infiltration.

TABLE 4.2

Azeotropes formed

| Azeotrope Component 1 | Azeotrope Component 2 | Azeotrope Component 3 | Relative Boiling point of Azeotrope at atmosphere conditions (C °) |
|---|---|---|---|
| Methanol | n-Hexane | | 50.6 |
| Ethanol | n-Hexane | Water | 56.0 |
| Ethanol | n-Hexane | | 58.7 |
| n-Hexane | Water | | 61.1 |

Specimens whose volume ranges from 1 mm$^3$ to 5000 mm$^3$ are placed in the reactor container 11. The reactor is sealed and a dissolving compound containing 650 grams of methanol, 400 grams of Ethanol, 1690 grams of toluene and 12 grams of lubricity additive are charged into the container at between 25 and 40° C. The operating parameters are employed as in Example 3. Azeotrope boiling points are given in Table 4.2.

Figure 7:
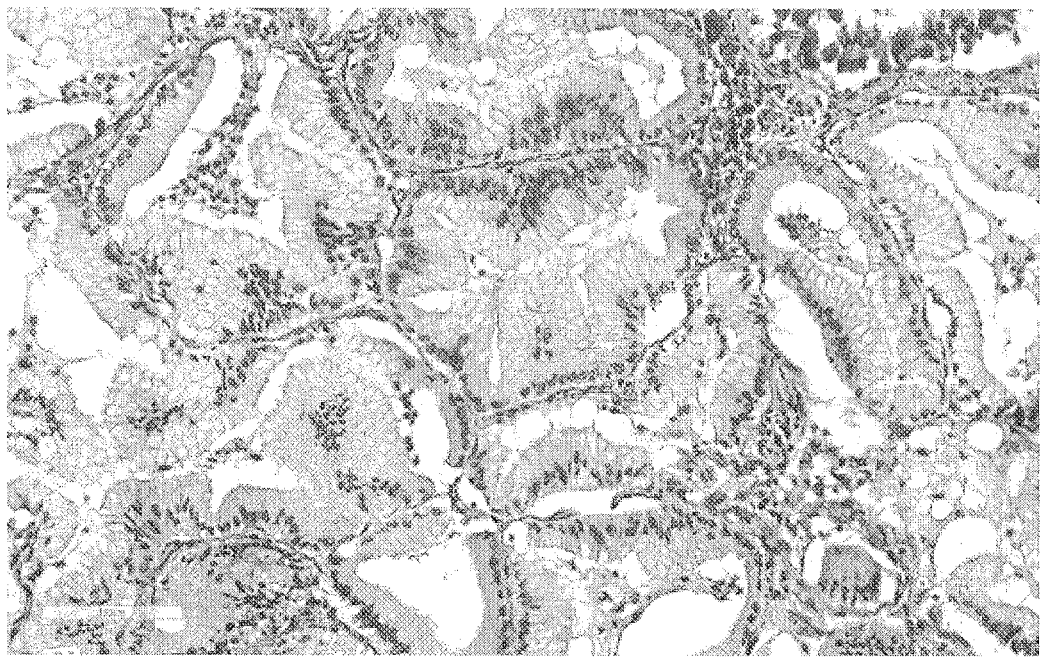
FIG. 7 shows an H&E Lung Adreno specimen processed using the azeotropically removed dissolving compound of Example 4.

FIG. 7 shows an H&E Lung Adreno specimen processed using the azeotropically removed dissolving compound components listed in Table 4.1. The results show excellent tissue preservation.

Figure 8:
FIG. 8 shows a specimen process using azeotropically removed dissolving compound of Example 5.

FIG. 8 illustrates a tissue section at room temperature 25° C. with lubricity additive and no ice cooling or skin refrigerant. The specimen is good for further histopathological procedures.

Example 5

A dissolving compound is selected to include the chemicals shown in Table 5.1 below.

TABLE 5.1

Selected dissolving compound

| Component | Relative Weight Percent |
|---|---|
| Methanol | 12 |
| tert-Butanol | 88 |

The operating parameters are employed as in Example 3. The dissolving compound is removed by vaporizing the methanol (i.e., zeotrope) and then the azeotrope shown in table 5.2. All gases formed in the reactor are removed using the vent.

TABLE 5.2

Zeotrope and Azeotrope used in tissue processing for example 5

| Component 1 | Component 2 | Component 3 | Relative Boiling point of Azeotrope at atmosphere conditions (C °) |
|---|---|---|---|
| Methanol | | | zeotrope |
| Tert-butanol | Water | | 79.9 |

Specimens whose volume ranges from 1 mm$^3$ to 5000 mm$^3$ are placed in the reactor container 11. The container is sealed and a dissolving compound containing 200 grams of methanol and 800 grams of tert-butanol is charged into the reactor container at between 30 and 40° C. The infiltrating medium is 9 parts Carbowax 4000 and 1 part Carbowax 1500. The operating parameters are employed as in Example 3. Azeotrope boiling points are given in Table 5.2.

Ketone/Hydrocarbon Dissolving Compounds

The dissolving compound can be selected to be a mixture of a ketone and a low molecular weight hydrocarbon which results in a simple three step procedure performed in a single container 11. First, the specimens are saturated with a mixture of a ketone/hydrocarbon dissolving compound, e.g., an acetone/hexane ("A/H") or an acetone/xylene ("A/X") mixture, to dissolve lipids and other cellular solutes. The container is then flooded with melted paraffin. In a last step, the dissolving compound mixture is removed from the container by draining and vaporization, allowing the melted paraffin to impregnate the specimens. Raw, i.e., non-processed and non-burred specimens up to 5 mm thick can be processed in about 60 minutes. A dissolving compound regenerator distills the evacuated dissolving compound, and converts vent waste gases into carbon dioxide and water through a thermocatalytic oxidizer.

The ketone/hydrocarbon dissolving compound embodiments may include a buffer to stabilize the extraction solvents to near neutral conditions. Tris-(hydroxymethyl) aminomethane is an excellent buffer for this application, but any compound capable of buffering the solvents at near neutral pH and which is soluble in the dissolving compound is applicable.

Other chemicals may be added to the A/H or A/X dissolving compound to increase viscosity. Examples include alcohols, ketones, aldehydes, solvents, and hydrocarbons, e.g. DMSO and 2-propanol. DMSO is an additional extraction solvent that can added to the A/H or A/X dissolving compound. DMSO assists in the extraction of large ring compounds and free nucleotides, e.g., lithocholic acid, deoxycholic acid, cholesterol, and other compounds that interfere with paraffin impregnation. Alcohols maybe added to slow the extraction process and prevent cellular membranes from rupturing.

Example 6

In this example, no Paraffin is directly added to the solvent mixture. Paraffin is used to displace the dissolving compound that has saturated the specimens. The impregnation takes an additional 20 minutes.

TABLE 6.0

Composition of Dissolving Compound

| Component | Weight-percent |
|---|---|
| Acetone | 59 |
| Hexane | 41 |

TABLE 6.1

Typical processing times and specimen type.

| Reference No. | Processing Time (minutes) | Impregnation Time (min) | Tissue Type |
|---|---|---|---|
| 501 | 10 | 50 | Breast tissue 2 mm |
| 502 | 10 | 50 | liver 2 mm |
| 503 | 10 | 50 | liver 2 mm |
| 504 | 20 | 50 | liver 5 mm |
| 505 | 30 | 50 | Breast tissue 5 mm |
| 506 | 30 | 50 | Breast tissue 5 mm |
| 507 | 20 | 50 | liver 5 mm |
| 508 | 30 | 50 | Breast tissue 4 mm |
| 509 | 30 | 50 | liver 10 mm |
| 510 | 30 | 50 | Liver 10 mm |
| 511 | 30 | 50 | Breast tissue 2 mm |
| 512 | 30 | 50 | Breast tissue 4 mm |

The dissolving compound of Table 6.0 is loaded into the solvent regenerator and heated for 15 minutes to an equilibrium temperature of 60° C. and a resulting pressure of about 0.8 bars (12 psig), then transferred to the reaction container 11 holding the specimens listed in Table 10.1.

The reaction container conditions are next equilibrated to 60° C., about 0.8 bars (12 psig), a flow rate of 2.35 liter/min, and a space velocity of 91.2-sec. Specimens are processed for individual times as indicated in Table 10.1. After this processing, specimens are super-saturated with the compound. The excess compound is then returned to the regenerator.

Paraffin is next charged into the reaction container. The container is stabilized to 60° C., and a chemical-potential difference is created between the paraffin and compound-saturated specimens. Vacuum is then used to increase this differential, vaporizing the compound within the specimen, and substituting compound molecules with hot paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

Example 7

The following is an example of batch solvent blending within the reaction container 11. Table 7.0 shows wt % of components before and after batch reactor blending.

TABLE 7.0

Solvent Batch blending Composition of Dissolving compound before and after.

| Component | Wt % Before Reactor Blending | Wt % After Reactor Blending |
|---|---|---|
| Acetone | 59.0 | 54.0 |
| Hexane | 41.0 | 38.0 |
| Paraffin | — | 8.0 |

TABLE 7.1

Typical processing times and specimen type.

| Reference No. | Processing Time (minutes) | Impregnation Time (min) | Tissue Type |
| --- | --- | --- | --- |
| 601 | 10 | 50 | Breast tissue 2 mm |
| 602 | 10 | 50 | liver 2 mm |
| 603 | 10 | 50 | liver 2 mm |
| 604 | 20 | 50 | liver 5 mm |
| 605 | 30 | 50 | Breast tissue 5 mm |
| 606 | 30 | 50 | Breast tissue 5 mm |
| 607 | 20 | 50 | liver 5 mm |
| 608 | 30 | 50 | Breast tissue 4 mm |
| 609 | 30 | 50 | liver 10 mm |
| 610 | 30 | 50 | Liver 10 mm |
| 611 | 30 | 50 | Breast tissue 2 mm |
| 612 | 30 | 50 | Breast tissue 4 m |

The dissolving compound residing in the solvent regenerator is conditioned by heating it to an equilibrium temperature of 60° C. and a pressure of about 0.8 bars (12 psig), then transferred to the reaction container 11 holding the tissue specimens. Any excess compound is returned to the solvent regenerator.

The reaction container conditions are next equilibrated to 60° C., about 1.6 bars (25 psig), a flow rate of 2.35 liter/min, and a space velocity of 91.2-sec. Specimens are processed for individual times as indicated in Table 7.1. After this processing, specimens are super-saturated with the dissolving compound.

Next, the reaction container is flooded with paraffin. The container is restabilized to 60° C., and a chemical-potential difference is created between the paraffin and the dissolving compound-saturated specimens. Vacuum is then used to increase this differential, vaporizing the compound within the specimens. The compound molecules are replaced with hot paraffin. Vacuum is continually applied until a pressure equilibration is achieved. Ten minutes after equilibrium is obtained, the heaters are disengaged, the vent solenoid opens, and the reaction container is brought to room temperature before extracting the specimens.

The present technique provides consistent, lifelike results, faster, without pre-processing requirement, with less cutting (often, specimens up to 5 mm thick can be processed), without solvent cross-contamination problems, without having to burr specimens, without water contamination problems, and in a single reaction container without the safety problems associated with microwave systems.

The present embodiments do not use microwaves to heat the specimen and does not use microwave reagents and thus do not suffer the disadvantages which plague microwave processing. Therefore, a homogeneous temperature throughout the reaction container can be readily maintained, and homogeneous temperature profiles can be seen between specimens and dissolving compound.

In the disclosed embodiments the presence of water in the dissolving compound does not affect the reactor container's temperature profile or the specimen's lifelike characteristics as can happen with microwave processing. Excess water from cellular solute extract and other cellular molecules can be further separated during solvent regeneration.

The solvent extraction process can take place in a single pressurized reactor container at pressures of between −29.9 inches Hg to 3.3 bars (50 psig), extraction temperatures between 30° C. and 100° C., and typical space velocities between 30 and 150 seconds.

In some embodiments paraffin need not be separated from the dissolving compound in a separate vessel, and there are no robotic or manual transfers of specimens.

In some embodiments the paraffin concentration in the dissolving compound can be allowed to increase over the life of the dissolving compound without affecting the lifelike characteristics of the specimens. In some embodiments the dissolving compound/paraffin blend can also be used to lubricate pumps used in the processor. In some embodiments the dissolving compound/paraffin blend can be chemically stable.

For many tissue types and sizes the specimen processing described above can be completed in approximately one hour. Specimens as large as 5 mm can be readily processed. There can be little or no significant pre-processing of specimens prior to dissolving compound extraction.

In some embodiments paraffin impregnation of the specimens does not require vacuum drying or transfer to another vessel prior to paraffin impregnation as with microwave processing. Specimen and dissolving compound temperatures can be homogenous within the reaction container once equilibrium has been reached.

Other tissue types can be processed using the present invention embodiments, such as but not limited to appendix, bowel, fallopian tube, kidney, liver, lung, parotid, placenta, prostate, thyroid, adenoma, cervix, skin and many others.

A number of embodiments of the invention have been described. Nevertheless, it will be understood that various modifications may be made without departing from the spirit and scope of the invention. Accordingly, other embodiments are within the scope of the following claims.

What is claimed is:

1. A process for preserving a specimen comprising: using a dissolving compound that can form a plural number of azeotropes; successively and azeotropically vaporizing off the formed azeotropes, the first formed azeotrope being vaporized off by reducing pressure, followed by raising temperature to form the second azeotrope, the second azeotrope being vaporized off by reducing pressure, followed by raising temperature to form the third azeotrope, and the third azeotrope being vaporized off by reducing pressure; wherein a first azeotrope is formed between one or more components of the dissolving compound and specimen-supplied water, a second azeotrope is formed between different components of the dissolving compound, and a third azeotrope is formed between different components of the dissolving compound, the third azeotrope being different from the second azeotrope; and impregnating the specimen with a support medium.

2. The process of claim 1, wherein the successively and azeotropically vaporizing off the azeotropes occurs at successively increasing boiling point temperatures.

3. The process of claim 1, wherein the azeotropes form at successively higher temperatures.

4. The process of claim 1, wherein the dissolving compound comprises methanol, tetrahydrofuran, toluene, and zinc acetate.

5. The process of claim 1, wherein the azeotropes formed comprise tetrahydrofuran-methanol, toluene-methanol, tetrahydrofuran-water, and toluene-water.

6. A process for preserving a specimen comprises:
dissolving and removing cellular solutes in the specimen using a dissolving compound;
partially removing the dissolving compound by forming two or more different azeotropes, at least two of the different azeotropes being formed with at least two component agents of the dissolving compound, and azeotropically vaporizing off the two or more different azeotropes, a first of the two or more different azeotropes being vaporized off by reducing pressure, followed by raising temperature to form a second of the two or more different azeotropes, the second of the two or more different azeotropes being vaporized off by reducing pressure; and replacing the solutes with an impregnated support medium.

7. The process of claim 6, performed in a continuous sequence of steps within a single vessel.

8. The process of claim 6, performed in the absence of formalin.

9. The process of claim 6, wherein the impregnated support medium comprises paraffin.

10. The process of claim 6, wherein the impregnated support medium is selected from the group consisting of: paraffin, plastic polymers, polyvinyl alcohol, polyethylene glycols, waxes, cellulose derivatives, agars, gels, and sugars.

11. The process of claim 1, wherein the dissolving compounds performs fixation, dehydration and clearing.

12. The process of claim 11, wherein the dissolving compounds facilitate infiltration of the support medium.

13. The process of claim 6, wherein the dissolving compounds performs fixation, dehydration and clearing.

14. The process of claim 13, wherein the dissolving compounds facilitate infiltration of the support medium.

* * * * *

UNITED STATES PATENT AND TRADEMARK OFFICE
CERTIFICATE OF CORRECTION

PATENT NO. : 10,365,189 B2
APPLICATION NO. : 14/706389
DATED : July 30, 2019
INVENTOR(S) : Wheeler It is certified that error appears in the above-identified patent and that said Letters Patent is hereby corrected as shown below:

In the Claims

In Claim 11, Column 21, Line 21, delete "performs" and insert -- perform --, therefor.

In Claim 13, Column 21, Line 25, delete "performs" and insert -- perform --, therefor.

Signed and Sealed this
Twenty-fourth Day of September, 2019

Andrei Iancu
*Director of the United States Patent and Trademark Office*